United States Patent [19]

Gilbertson

[11] 4,366,320

[45] Dec. 28, 1982

[54] 4-SUBSTITUTED PHENYL-1,2,4-TRIAZOLINE-3,5-DIONES AND THEIR DIHYDRO ANALOGS AS ANALYTICAL REAGENTS

[75] Inventor: Terry J. Gilbertson, Kalamazoo, Mich.

[73] Assignee: The Upjohn Company, Kalamazoo, Mich.

[21] Appl. No.: 174,050

[22] Filed: Jul. 31, 1980

[51] Int. Cl.$^3$ .................... B65D 71/00; G01N 31/22; G01N 33/50; C07D 249/12
[52] U.S. Cl. .................................. 548/264; 206/569; 544/234; 560/15; 560/158; 436/106
[58] Field of Search ........................................ 548/264

[56] References Cited

U.S. PATENT DOCUMENTS

| | | | |
|---|---|---|---|
| 3,912,735 | 10/1975 | Von Bredow et al. | 548/264 |
| 3,966,530 | 6/1976 | Cutts et al. | 548/264 |
| 4,087,534 | 5/1978 | Ovadia et al. | 548/264 |
| 4,249,934 | 2/1981 | Wakabayashi et al. | 548/264 |

*Primary Examiner*—Alton D. Rollins
*Attorney, Agent, or Firm*—L. Ruth Hattan; Robert A. Armitage

[57] ABSTRACT

A novel reagent useful for preparing adducts of diene so that the diene may be assayed by gas liquid chromatography utilizing an electron capture detection system.

6 Claims, No Drawings

4-SUBSTITUTED PHENYL-1,2,4-TRIAZOLINE-3,5-DIONES AND THEIR DIHYDRO ANALOGS AS ANALYTICAL REAGENTS

DESCRIPTION

BACKGROUND OF INVENTION

The discovery of various metabolites of Vitamin $D_3$ has led to clinical studies assessing the significance of the presence or absence of these metabolites in various diseases and conditions. In order to properly evaluate the effect of the metabolite on the course of the disease, an appropriate detection and measurement system for the metabolites must be available. The normal level of $1\alpha,25$-dihydroxycholecalciferol ($1\alpha,25$-diOH Vit $D_3$) in man is 50–100 picograms. This low quantity of substance is extremely difficult to measure with an accuracy sufficient to see if there is an effect on the course of a disease or conditions due to the presence or absence of this material. Although certain diagnostic tests are available, they have been insufficciently sensitive and reproducible at the very low levels of substance being measured. A new reagent has been discovered which allows the sensitive, reproducible measurement of $1\alpha,25$-diOH Vit $D_3$ and related compounds at very low concentrations.

PRIOR ART

Unsubstituted 4-phenyl-1,2,4-triazoline-3,5-diones and their related urazoles are known in the art, J. Org. Chem., 31, 3444 (1966). This reference also discloses that the urazoles are oxidized to the triazolines by nitrogen dioxide. The urazoles are generally prepared by reacting N-halo ethyl carbazide with aniline, J. Am. Chem. Soc., 89, 1417 (1966), to form an open chain amide which is cyclized to the 4-phenyl urazoles by strong base and heat, Arch. Pharm., 294, 370 (1961). The 4-phenyl-1,2,4-triazole-3,5-dione has been reacted with Vitamin $D_3$ and forms an adduct. No utility for the adduct is disclosed in the reference, J. Org. Chem., 41, 2098 (1976) although there appears to be interest in synthesizing hydroxylated Vitamin $D_3$ through this adduct. However, the expected product was not obtained upon hydrolysis.

Gas liquid chromatography has been used to separate Vitamin D compounds.

An electron capture sensitivity comparison of various derivatized primary and secondary amines has been studied using some fluorinated derivatives. In the selection of a reagent, the entire structure of the derivative should be studied, J. of Pharm. Sci., 61, 1235 (1972).

SUMMARY OF THE INVENTION

In accordance with this invention there are 4-(fluorinated phenyl)-1,2,4-triazoline-3,5-diones and related urazoles of the structure of Formula 1, see Table I, wherein A is N=N or

H H

N—N and X is fluoro and n is an integer of one through 5 or $X_{(n)}$ is 4'-trifluoromethyl.

A further part of the invention is the adduct addition product between the 4-(fluorinated phenyl)-1,2,4-triazoline-3,5-dione of Formula 1 and $1\alpha,25$-diOH Vit $D_3$, see Figure 2 of Chart, $X_{(n)}$ defined as above. Adduct formation is additionally significant for other dienes such as Vitamin $D_3$, 24,25-diOH Vit $D_3$, 25-OH Vit $D_3$ and leukotriene B.

Another portion of the invention is a method for assaying levels of $1\alpha,25$-diOH Vit $D_3$ which comprises reacting the $1\alpha,25$-diOH Vit $D_3$ in a sample with a compound of Figure 1 wherein A is N=N, thereby forming an adduct of Figure 2, detecting the quantity of adduct present with an electron capture detection system preceded by separation in gas-liquid chromatography and comparing the quantity detected with a standard curve.

Another aspect of the invention is a kit which comprises in a container a compound of Figure 1 wherein A is N=N or

H H

N—N and $1\alpha,25$-diOH Vit $D_3$.

DETAILED DESCRIPTION OF THE INVENTION

The reagent, Formula I compound wherein A is N=N, used to derivatize the $1\alpha,25$-diOH Vit $D_3$ is prepared generally through well known reactions, specifically those set out in the Prior Art portion of this specification. The pentafluoro compound is prepared through a different cyclizing reagent than the strong base ordinarily used. When the strong base is employed for cyclization of the pentafluoro ethoxy carbazide, a urazole is prepared. However, the p-position of the phenyl ring is substituted by hydroxy rather than fluoro. In order to prepare the pentafluoro substituted urazole, a weak base, particularly potassium carbonate, must be employed. The preferred compound employed in the electron capture detection assay for $1\alpha,25$-diOH Vit $D_3$ is the pentafluoro substituted compound of Figure 1 wherein A is N=N.

The reagent of Formula 1 wherein A is N=N should react with a diene system in a Diels Alder type diene-dienophile reaction to form an adduct as shown in Formula 2. Other dienes which would have significance as to quantity present in a sample include Vitamin $D_3$, 25-hydroxycholecalciferol, 24,25-dihydroxycholecalciferol and leukotriene B. Preferred dienes for adduct formation and measurement by an electron capture detection system are $1\alpha,25$-diOH Vit $D_3$, Vitamin $D_3$ and leukotriene B. The sample employed need not be from a biological system but can be from any other system in which analysis is significant. For example, Vit $D_3$ analysis in certain food products is quite important. The adduct is formed by simply combining the particular diene and compound of Formula 1 wherein A is N=N in a solvent such as ethyl acetate or other organic solvent which places the reactants into solution at a temperature of from about 0° to about 50° C. The adduct can be isolated from solution and used as the standard in the gas chromatographic electron capture system or this reaction carried out on the diene present in the sample being tested. The volatility of the adduct may be appreciably increased by making a derivative having certain groups. For example, the $1\alpha,25$-diOH Vit $D_3$ adduct is easily silylated which provides an adduct with markedly greater volatility.

The silylated adduct is then injected into a standard gas liquid phase chromatograph using a 0.25% to 3% methyl silicone liquid phase on a diatomaceous earth column at a temperature of about 280° to about 320° C. A nickel electron capture detection system is employed. Other electron capture systems which can withstand the high temperatures of the system can be employed.

The following examples are illustrative of the scope of this invention. They are not intended to narrow the scope of the generic invention but merely to exemplify.

Reagent Preparation

EXAMPLE 1

4-(Pentafluorophenyl)-urazole a. 2-Carbethoxyhydrazinecarbonyl chloride

A one-liter flask is fitted with a gas-dispersion tube, a 500 ml dropping funnel, a stirrer and a condenser fitted with a drying tube. The gas-dispersion tube is connected to a laboratory tank of phosgene on a pan balance. Dry ether, 200 ml, is placed in the flask. The flask is cooled with an ice bath. Phosgene, 115 g (1.2 M) is run into the ether. Ethylcarbazate, 24 g (0.24 M), is added to 500 ml of ether and placed in the dropping funnel. The solution of ethylcarbazate is added slowly and when addition is complete, the reaction is allowed to stir overnight. The solution is filtered and the solvent and excess phosgene removed with a vacuum pump fitted with a dry-ice trap. The trapped phosgene is destroyed by addition to a mixture of $NaHCO_3$ solution and ice. The product is a white powder which is redissolved in ether and filtered. The ether is evaporated resulting in a crystalline white solid weighing 38 g, mp 77°–80°.

b. 4-(Pentafluorophenyl)-1-carbethoxysemicarbazide

Pentafluoroaniline (17 g, 0.106 mol) is dissolved in 300 ml of toluene with heating. The 2-carbethoxyhydrazinecarbonyl chloride, 19.4 g (0.122 M) is added to the hot solution. The mixture is refluxed until a white solid precipitates. The solid is filtered to give 24.8 g. The product is crystallized by dissolving in ethyl acetate/toluene (½ by vol) and evaporating until crystals appear, mp 180°–182°.

Anal. Calcd for $C_{10}H_8F_5N_3O_3$: C, 38.34; H, 2.55; N, 13.52. Found: C, 38.44; H, 2.66, N, 13.67. MS Calcd: m/e 313. Found: 313.

c. 4-(Pentafluorophenyl)-urazole 4-(Pentafluorophenyl)-1-carbethoxysemicarbazide, 2.13 g (0.0068 M), and potassium carbonate, 0.938 g (0.0068 M), are added to 75 ml of water. The mixture is heated at 70° C. under $N_2$ about 12 hours. The solution is cooled in an ice bath and filtered to remove a trace of starting material. The pH of the solution is adjusted to pH 7 with concentrated HCl and extracted with ethyl acetate to remove a product which is less polar than the urazole in the TLC system, chloroform/ethyl acetate/acetic acid (5/5/1). The pH of the solution is reduced to 1 or 2 with concentrated HCl and then extracted with ethyl acetate. About ⅓ of a volume of toluene is added to the ethyl acetate and the solvents evaporated. The resulting crude solid weighs 0.569 g. The product is purified by two crystallizations from ethyl acetate/toluene (½ by vol). The yield of purified material is 0.476 g. It is recrystallized from $H_2O$, mp 223°–226°.

Anal. Calcd for $C_8H_2F_5N_3O_2$: C, 35.97; H, 0.754; N, 15.73. Found: C, 36.29; H, 0.91; N, 15.67. MS Calcd: m/e 267. Found: 267.

EXAMPLE 2

4-(Pentafluorophenyl)-1,2,4-triazoline-3,5-dione

A 50 ml, three-necked flask is fitted with a gas-dispersion tube, a drying tube and a stirrer. 4-(Pentafluorophenyl)urazole, 0.5 g (1.8 mM) is dissolved in 25 ml of ethyl acetate. Anhydrous sodium sulfate, 3 g, is added to remove water present in $NO_2$. The reaction mixture is cooled in an ice bath, and nitrogen dioxide added slowly for 20 minutes. The mixture is allowed to stir for 20 minutes. The $Na_2SO_4$ is removed by filtration and the ethyl acetate removed with the rotary evaporator to yield a red oil. The residual solvent is removed with a vacuum pump to yield a crystalline solid, 0.35 g, mp 88°–91° C. The product is further purified by sublimation, mp 94°–96° C.

Anal. Calcd for $C_8F_5N_3O_2$: C, 36.23. Found: C, 37.15. MS Calcd: m/e 265. Found: m/e 209.

EXAMPLE 3

4-(2',4',6'-Trifluorophenyl)-urazole a. 4-(2',4',6'-Trifluorophenyl)-carbethoxysemicarbazide A toluene solution of 2,4,6-trifluoroaniline is reacted with 2-carbethoxyhydrazinecarbonyl chloride as described above in Example 1b, mp 177°–178° (ethyl acetate/toluene).

Anal. Calcd for $C_{10}H_{10}F_3N_3O_3$: C, 43.32; H, 3.61; N, 15.16 Found: C, 43.62; H, 3.73; N, 15.19. MS Calcd: m/e 277. Found: 277.

IR and NMR are consistent with the structure.

b. 4-(2',4',6'-Trifluorophenyl)-urazole

This compound is prepared in a similar fashion to Example 1c except that 3 N KOH is employed as the base and that the desired compound precipitates after the reaction mixture is acidified. It is recrystallized from $H_2O$, mp 221°–222°.

Anal. Calcd. for $C_8H_4F_3N_3O_2$: C, 41.56; H, 1.73; N, 18.18. Found: C, 41.79; H, 1.76; N, 18.16. MS Calcd: m/e 231. Found: 231.

EXAMPLE 4

4-(2',4',6'-Trifluorophenyl)-1,2,4-triazoline-3,5-dione

This triazoline dione is prepared in the same manner as described for Example 2, mp 99°–100°.

Anal. Calcd for $C_8H_2F_3N_3O_2$: C, 41.92; H, 0.87. Found: C, 42.14; H, 1.16. MS Calcd: m/e 229. Found: 173.

IR was consistent with the structure.

EXAMPLE 5

4-(4'-Trifluoromethylphenyl)-urazole a. 4-(4'-Trifluoromethylphenyl)-1-carbethoxysemicarbazide This compound is prepared by the same procedure used for the other semicarbazides, mp 205°–208° (ethyl acetate/toluene).

Anal. Calcd for $C_{11}H_{12}F_3N_3O_3$: C, 45.36; H, 4.12; N, 14.43. Found: C, 45.31; H, 4.20; N, 14.62. MS Calcd: m/e 291. Found: 291.

b. 4-(4'-Trifluoromethylphenyl)-urazole

This urazole is prepared in the same way as Example 3b, yield 61.9%. It is crystallized from H$_2$O, mp 229°–230°.

Anal. Calcd for C$_9$H$_6$F$_3$N$_3$O$_2$: C, 44.08; H, 2.45; N, 17.14. Found: C, 44.07; H, 2.46; N, 17.16. MS Calcd: m/e 245. Found: 245.

EXAMPLE 6

4-(4'-Trifluoromethylphenyl)-1,2,4-triazoline-3,5-dione

This triazoline dione is also prepared in the same manner, as Example 2, mp, turns to yellow compound perhaps a polymer at 155°–160°. The yellow compound does not melt at 350°.

Anal. Calcd for C$_9$H$_4$F$_3$N$_3$O$_2$: C, 44.44; H, 1.65. Found: C, 44.02; H, 1.90.

ADDUCT PREPARATION

EXAMPLE 7

Adduct Formation Using 4-pentafluorophenyl-1,2,4-triazoline-3,5-dione and 1α,25-diOH Vit D$_3$ The dry residue from a standard solution or a purified fraction containing the 1α,25-diOH Vit D$_3$ is dissolved in 100 μl of ethyl acetate. A solution of 4-pentafluorophenyl-1,2,4-triazoline-3,5-dione (3 mg/ml) is prepared. Then 100 μl of the dione solution in ethyl acetate is added to the ethyl acetate solution containing the 1α,25-diOH Vit D$_3$. The mixture is allowed to sit at room temperature for one to 4 hours.

EXAMPLE 8

Gas Liquid Chromatography with Nickel Electron Capture Detection System a. Silylization of Adduct of Example 7

The adduct prepared in Example 7 is then silylated by the addition of 50 μl of a mixture of trimethylsilylimidazole, trimethylsilyl acetamide and trimethylchlorosilane (3:3:2) (obtained from Pierce Chemical with the name Tri-Sil/TBT ®). This mixture is allowed to sit for one hour at room temperature.

b. Chromatographic Procedure

The silylated reaction mixture is then made up to one ml volume with hexane. The excess derivatizing reagents are removed by the addition of 0.5 ml of 50% NH$_4$OH. If the sample size is 1 μg or greater, 10 μl or less of the above hexane solution can be injected directly into the gas liquid chromatograph. If it is smaller, the aqueous layer is frozen and the hexane layer is poured off. The hexane layer is then concentrated to an appropriate volume.

An aliquot of the final hexane solution (one to 10 μl) containing the silylated adduct of 1α,25-diOH Vit D$_3$ is injected into the gas chromatograph through a teflon lined high temperature septum onto a 1½ foot packed column. The column packing is 3% methyl silicone or 1% methyl silicone on purified diatomaceous earth. The following conditions are used with these columns: injection temperature, 310° C., column temperature, 300° C. and detector temperature, 320° C. The flow rate of the 95%/5% Argon/Methane carrier is 20 ml/min. The attenuation setting is 128 for a sensitivity of 20 pg on column and 32 for a sensitivity of 10 pg on column. The retention times for the silylated adduct are about 12 minutes with the 3% column and about 4 minutes with the 1% column. A $^{63}$Ni electron capture detector is employed.

EXAMPLE 9

The gas liquid chromatographic assay is performed with any of the specific dienes mentioned previously, i.e., Vit D$_3$, 24-25-diOH Vit D$_3$, 25-OH Vit D$_3$ and leukotriene B. With any of these dienes the dienophile is any of the previously mentioned 1,2,4-triazoline-3,5-diones, specifically the 2',4',6'-trifluoro, 2',4'-difluoro, and the 4'-trifluoromethyl compounds. Similar assay results are achieved.

TABLE I

Formula 1: [structure of X$_{(n)}$-phenyl-N bonded to two C=O groups with A bridge]

Formula 2: [vitamin D$_3$ adduct structure with X$_{(n)}$-phenyl-triazoline]

I claim:

1. A compound of the formula

[structure of X$_{(n)}$-phenyl-N bonded to two C=O groups with A bridge]

wherein X$_{(n)}$ is pentafluoro; 2',4',6'-trifluoro; or 4'-trifluoromethyl; and A is N═N or $$\begin{array}{cc} H & H \\ | & | \\ N{-}N; \end{array}$$

with the proviso that when X$_{(n)}$ is 2',4',6'-trifluoro or 4'-trifluoromethyl, A is N═N.

2. A compound in accordance with claim 1 wherein X$_{(n)}$ is pentafluoro.

3. A compound in accordance with claim 1 wherein X$_{(n)}$ is 4'-trifluoromethyl.

4. A compound in accordance with claim 1 wherein X$_{(n)}$ is 2',4',6'-trifluoro.

5. A compound in accordance with claim 2 wherein A is $$\begin{array}{cc} H & H \\ | & | \\ N{-}N. \end{array}$$

6. A compound in accordance with claim 2 wherein A is N═N.